United States Patent

Braña Fernández et al.

[11] Patent Number: 5,552,544
[45] Date of Patent: Sep. 3, 1996

[54] 5-NITROBENZO[DE]ISOQUINOLINE-1,3-DIONES THEIR PREPARATION AND THEIR USE

[76] Inventors: Miguel Braña Fernández; José M. Castellano Berlanga, both of Avenida de Burgos No. 20, 1ºM., ES-28036, Madrid; Marina Morán Moset, 50 Calle Gaztambide, ES-28015 Madrid, all of Spain; Erich Schlick, 4½ Rudolph-Wihr-Strasse, 6708 Neuhofen; Gerhard Keilhauer, 20 Industriestrasse, 6701 Dannstadt-Schauernheim, both of Germany

[21] Appl. No.: 533,944

[22] Filed: Jun. 4, 1990

Related U.S. Application Data

[60] Continuation of Ser. No. 213,690, Jun. 30, 1988, abandoned, which is a division of Ser. No. 110,871, Oct. 21, 1987, abandoned.

Foreign Application Priority Data

Oct. 21, 1986 [DE] Germany .......................... 36 35 711.1

[51] Int. Cl.⁶ ..................... C07D 413/06; C07D 221/14; A61K 31/44; A61K 31/535
[52] U.S. Cl. ............................................. 544/126; 546/100
[58] Field of Search ............................... 546/100; 544/126

[56] References Cited

U.S. PATENT DOCUMENTS 4,204,063  5/1980  Brana ........................ 546/100
4,614,820  9/1986  Zee-Ching ................. 546/99
4,782,064  11/1988  Wright ....................... 546/100

OTHER PUBLICATIONS

Paull et al. Arzneim. Forsch./Drug Res. 34 (II) (1984), 1243–1246.

Primary Examiner—Mark L. Berch
Attorney, Agent, or Firm—Keil & Weinkauf

[57] ABSTRACT

An antitumor 5-nitrobenzo[de]isoquinoline-1,3-dione of the formula I

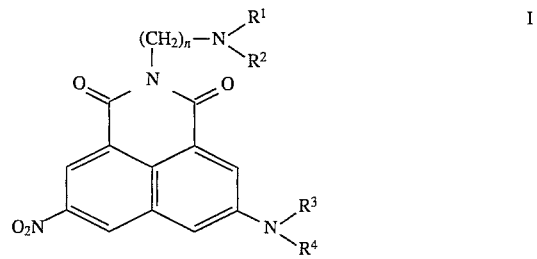

where n is 1 or 2, $R^1$ and $R^2$ are identical or different and are each hydrogen, $C_1$–$C_6$-alkyl, $C_1$–$C_6$-hydroxyalkyl, pyrrolidinyl, morpholino, piperidinyl or piperacinyl and $R^3$ and $R^4$ are identical or different and are each hydrogen, $C_1$–$C_6$-alkyl, $C_1$–$C_6$-acyl, $C_2$–$C_7$-alkoxycarbonyl, ureyl, aminocarbonyl or $C_2$–$C_7$-alkylaminocarbonyl, and its salts with physiologically tolerated acids, are described.

4 Claims, No Drawings

5-NITROBENZO[DE]ISOQUINOLINE-1,3-DIONES THEIR PREPARATION AND THEIR USE

This application is a continuation of Ser. No. 07/213,690, filed Jun. 20, 1988, now abandoned which is a divisional of Ser. No. 110,871, filed Oct. 21, 1987 now abandoned.

The present invention relates to novel 5-nitro-benzo[de] isoquinolines, processes for their preparation, and their use for the treatment of diseases.

It is known that certain benzo[de]isoquinolines have antitumor properties (Arzneim, Forsch./Drug Res. 34 (II) (1984), 1243). However, the action of these compounds is not satisfactory in every respect.

We have found that 5-nitrobenzo[de]isoquinoline-1,3-diones of the formula I

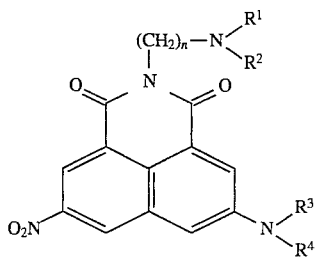

where n is 1 or 2, $R^1$ and $R^2$ are identical or different and are each hydrogen, $C_1$–$C_6$-alky, $C_1$–$C_6$-hydroxyalkyl, or $R^1$ and $R^2$ together with the N-atom can form a pyrrolidinyl, morpholino, or piperidinyl and $R^3$ and $R^4$ are identical or different and are each hydrogen, $C_1$–$C_6$-alkyl, $C_1$–$C_6$-acyl, $C_2$–$C_7$-alkoxycarbonyl, ureyl, aminocarbonyl or $C_2$–$C_7$-alkylaminocarbonyl, and their salts with physiologically tolerated acids have a better action and a better action spectrum as antitumor substances.

Preferred compounds are those in which $R^1$ and $R^2$ are each methyl or ethyl, $R^3$ is hydrogen or $C_1$–$C_6$-acyl, in particular acetyl, and $R^4$ is hydrogen.

Suitable physiologically tolerated acids for salt formation are organic and inorganic acids, such as hydrochloric acid, sulfuric acid, phosphoric acid, acetic acid, citric acid, oxalic acid, malonic acid, salicylic acid, maleic acid, fumaric acid, succinic acid, ascorbic acid, malic acid, methanesulfonic acid, isethionic acid, lactic acid, gluconic acid, glucuronic acid, amidosulfonic acid, benzoic acid, tartaric acid and pamoic acid.

The novel compounds may be in the solvated form. Such forms can form, for example, with water or ethanol.

The novel compounds are prepared by a process in which
a) a 3-nitro-1,8-naphthalic anhydride of the formula II

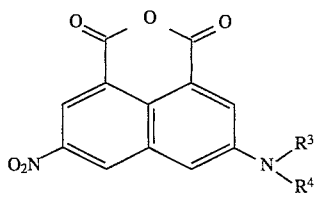

where $R^3$ and $R^4$ have the stated meanings, is reacted with an amine of the formula III

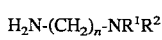

where n, $R^1$ and $R^2$ have the stated meanings or b) a 5,8-dinitrobenzo[de]isoquinoline of the formula IV

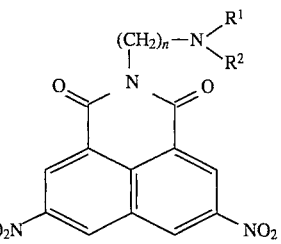

where n, $R^1$ and $R^3$ have the stated meanings, is selectively reduced and, if required, the resulting 5-nitro-8-amino derivative is alkylated or acylated, and the resulting compound is, if required, converted to its salts with physiologically tolerated acids.

The reaction according to a) is carried out in a suitable solvent, such as methanol, ethanol, propanol or acetone, as a rule at room temperature. The compound according to the invention separates out of the reaction mixture and can be purified by chromatography and/or by recrystallization.

The reduction according to b) may be effected with an alkali metal hydride or polysulfide or tin(II) chloride or by catalytic hydrogenation with the calculated amount of hydrogen. The amines thus obtained can, if desired, then be alkylated or acylated or reacted with an alkyl or metal isocyanate in a conventional manne.

The compounds thus obtained can be converted to their salts in a conventional manner, for example by reaction with an acid.

The compounds according to the invention can be administered in a conventional manner, orally or parenterally. They can be used in the conventional solid or liquid pharmaceutical form, for example as tablets, film tablets, capsules, granules, coated tablets or solutions. These are prepared in a conventional manner, and to do so the active compounds are mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or antioxidants (cf. H. Sucker et al.: Pharmazeutische Technologie, Thieme-Verlag, Stuttgart, 1978). The administration forms thus obtained normally contain the active compound in an amount of from 10 to 90% by weight, The cytotoxicity of the novel compounds was determined as follows:

$5 \times 10^3$ human tumor cells in a state of exponential growth were plated out in 125 μl of complete growth medium (MEM with Earle's salts+10% of FCS, Flow Laboratories, Meckenheim, FRG) in 96-well plates and incubated overnight at 37° C. in the presence of 5% of $CO_2$ in a water vapor-saturated atmosphere. The substance was added on the next day in 25 μl of complete culture medium per culture well, The final concentration was $10^{-4}$ mole of protein per well; titration was carried out twice serially with double determination. The following controls were set up on each culture plate: a) culture medium only; b) cells with culture medium but without active compound; c) a titrated reference standard substance of known biological activity. After incubation for a further 72 hours under the above conditions, the surviving cells were stained with a crystal violet solution (15 g of crystal violet, 7 g of NaCl, 646 ml of ethanol and 172.8 ml of 37% strength formaldehyde made up to 2 1 with $H_2O$). For this purpose, the cells were stained for 20 minutes with 50 μl of the stain solution at room temperature after the culture medium had been removed. The culture plates were then washed with water in order to remove stain which was not bound to the cells. After the addition of 100μl of measuring solution (50% of ethanol and 0.1% of acetic acid), the cell-bound stain was determined photometrically at 540 nm with the aid of a Titertek Multiscan MCC/340 (FLow Laboratories, Meckenheim). The concentrations of substance which produce 50% lysis of the cells compared with the untreated control cells (measured via the decrease in absorption) were stated.

In this test, the novel compounds, in particular the substance of Example 1, had a good action.

EXAMPLE 1

1.16 g (0.01 mole) of N,N-diethyl-1,2-diaminoethane were added to 2.58 (0.01 mole) of 6-amino-3-nitro-1,8-naphthalic anhydride in 20 ml ethanol, The mixture was stirred for 6 hours and left to stand overnight, The precipitated product was filtered off under suction, chromatographed over silica gel with a 7:10 CHCl$_3$/CH$_3$OH mixture and recrystallized from methanol/water. 8-Amino-2-[2-(diethylamino)ethyl]-5-nitrobenzo[de]isoquinoline-1,3-dione of melting point 174° C. (toluene) was obtained.

EXAMPLE 2

4.7 g of tin(II) chloride were suspended in 8.7 ml of hot glacial acetic acid, and the suspension was cooled to 0° C. while passing in hydrogen chloride. The solution thus obtained was added to a solution of 2 g (0.005 mole) of 2-[2-(dimethylamino)-ethyl]-5,8-dinitrobenzo[de]isoquinoline-1,3-dione in hot glacial acetic acid and the mixture was stirred for 45 minutes at below 30° C. The mixture was left to stand overnight, after which 1 ml of water was added to the slurry-like product at 70° C. The major part of the glacial acetic acid was stripped off from the reaction mixture under reduced pressure. The residue was washed with water, and 28 ml of 20% strength sodium hydroxide solution were added, the temperature not exceeding 25° C. The resulting solid product was filtered off and washed with boiling 10% strength hydrochloric acid until the wash liquid no longer gave a precipitate when ammonia was added. The 8-amino-2-[2-(dimethylamino)-ethyl]-5-nitrobenzo[de]isoquinoline-1,3-dione was chromatographed over silica gel using a 7:10 CHCl$_3$/CH$_3$OH mixture and recrystallized from toluene. The melting point was 266°–268° C.

The following were prepared similarly to Examples 1 and 2:

3. 8-Amino-5-nitro-2-[2-(pyrrolidinyl)-ethyl]-benzo[de]isoquinoline-1,3-dione, mp. 320° C. (toluene).

4. 8-Amino-5-nitro-2-[2-(piperidinyl)-ethyl]-benzo[de]isoquinoline-1,3-dione, mp. 232°–234° C. (toluene).

5. 8-Amino-2-[3-[di-(2-hydroxyethyl)-amino]-propyl]-5-nitrobenzo[de]-isoquinoline-1,3-dione, mp. 151°–152° C. (toluene).

6. 8-Amino-2-[2-(2-hydroxyethyl)-aminoethyl]-5-nitrobenzo[de]isoquinoline-1,3-dione, mp. >280° C. (dimethylformamide/water).

7. 8-Amino-2-[2-[di-(2-hydroxyethyl)-amino]-ethyl]-5-nitrobenzo[de]isoquinoline-1,3-dione, mp. >280° C. (dimethylformamide/water).

8. 8-Amino-2-[2-(morpholino)-ethyl]-5-nitrobenzo[de]-isoquinoline-1,3-dione, mp. 234° C. (toluene).

9. 8-Ethoxycarbonylamino-2-[2-(dimethylamino)-ethyl]-5-nitrobenzo[de]isoquinoline-1,3-dione, mp. >320° C. (glacial acetic acid).

EXAMPLE 10

3.54 g (0.01 mole) of 8-amino-5-nitro-2-[2-(pyrrolidinyl)-ethyl]-benzo[de]isoquinoline-1,3-dione (cf. Example 3) and 3.05 g (0.05 mole) of ethyl isocyanate in 50 ml of benzene were refluxed for 2 hours. The precipitated 8-ethylaminocarbonylamino-5-nitro-2-[2-(pyrrolidinyl)-ethyl]-benzo[de]-isoquinoline-1,3-dione was filtered off and recrystallized from ethanol. The melting point was 234° C.

The following was prepared similarly to Example 10:

11. 8-Ethylaminocarbonylamino-5-nitro-2-[2-dimethylamino-ethyl)-benzo[de]isoquinoline-1,3-dione, mp. 166° C. (ethyl acetate).

EXAMPLE 12

A mixture of 3.28 g (0.01 mole) of 8-amino-2-[2-(dimethylamino)-ethyl]-5-nitrobenzo[de]isoquinoline-1,3-dione (cf. Example 2), 10 ml of acetyl chloride and 20 ml of acetic anhydride was refluxed for 1 hour, while stirring. After cooling, the reaction mixture was poured onto 50 g of ice and neutralized with sodium bicarbonate. The precipitated 8-acetylamino-2-[2-(dimethylamino)-ethyl]-5-nitrobenzo[de]isoquinoline-1,3-dione was filtered off and recrystallized from dimethylformamide/water. The melting point was 320° C. (glacial acetic acid),

We claim:

1. A 5-nitrobenzo(de)isoquinoline-1,3-dione of the formula I

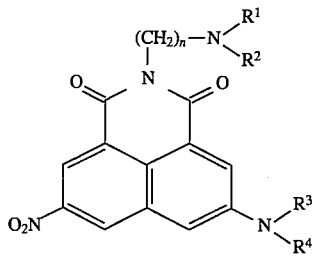

where n is 1 or 2, $R^1$ and $R^2$ are identical or different and are each hydrogen, $C_1$–$C_6$-alkyl or $C_1$–$C_6$-hydroxyalkyl, and $R^3$ and $R^4$ are each hydrogen, or one is hydrogen and the other is $C_1$–$C_6$-alkyl, $C_1$–$C_6$-acyl, $C_2$–$C_7$-alkoxycarbonyl, aminocarbonyl or $C_2$$C_7$-alkylaminocarbonyl; or $R^1$ and $R^2$ together with the N atom form a pyrrolidinyl, morpholino or piperidinyl group where $R^1$ and $R^4$ are both hydrogen; or $R^1$ and $R^2$ together with the N atom form a pyrrolidinyl group where $R^3$ is hydrogen and $R^4$ is ethoxycarbonylamino; and its salts with physiologically tolerated acids.

2. A compound as defined in claim 1 wherein $R^1$ and $R^2$ are each methyl or ethyl and $R^3$ and $R^4$ are each hydrogen.

3. An 8-amino-2-(2-(dimethylamino)-ethyl)-5-nitrobenzo(de)isoquinoline-1,3-dione.

4. A 5-nitrobenzo(de)isoquinoline-1,3-dione selected from the group consisting of 8-amino-2-(2-(diethylamino)-ethyl)-5-nitrobenzo(de)isoquinoline-1,3-dione, 8-amino-5-nitro-2-(2-(pyrrolidinyl)-ethyl)-benzo(de)isoquinoline-1,3-dione, 8-amino-2-(2-(di)-2-hydroxyethyl)-amino)-ethyl)-5-nitrobenzo(de)isoquinoline-1,3-dione, 8-amino-2-(2-(morpholino)-ethyl)-5-nitrobenzo(de)-isoquinoline-1,3-dione, 8-ethoxy-carbonylamino-2-(2-(dimethylamino)-ethyl)-5-nitrobenzo(de)iso-quinoline-1,3-dione, 8-ethylaminocarbonyl-amino-5-nitro-2-(2-(pyrrolidinyl)-ethyl)-benzo(de)isoquinoline-1,3-dione, 8-ethylaminocarbonylamino-5-nitro-2-(2-dimethylaminoethyl)-benzo(de)isoquinoline-1,3-dione, and 8-acetylamino-2-(2-(di-methylamino)-ethyl)-5-nitrobenzo(de)isoquinoline-1,3-dione and its salts with physiologically tolerated acids.

* * * * *

UNITED STATES PATENT AND TRADEMARK OFFICE
CERTIFICATE OF CORRECTION

PATENT NO.: 5,552,544

DATED: September 3, 1996

INVENTOR(S): BRANA et al.

It is certified that error appears in the above-identified patent and that said Letters Patent is hereby corrected as shown below:

On the cover page, "Braña Fernández et al." should be --Braña et al.--.

On the cover page, item [76], the first listed inventor's name "Miguel Braña Fernández" should be --Miguel F. Braña--.

Column 4, claim 1, line 43, "R$^1$" should be --R$^3$--.

Signed and Sealed this

Nineteenth Day of November, 1996

*Attest:*

BRUCE LEHMAN

*Attesting Officer*    Commissioner of Patents and Trademarks